United States Patent [19]

Ryan

[11] Patent Number: 4,959,204

[45] Date of Patent: * Sep. 25, 1990

[54] ORAL COMPOSITIONS

[75] Inventor: Leslie D. Ryan, Millville, Ohio

[73] Assignee: The Proctor & Gamble Company, Cincinnati, Ohio

[ * ] Notice: The portion of the term of this patent subsequent to May 4, 2004 has been disclaimed.

[21] Appl. No.: 10,253

[22] Filed: Feb. 2, 1987

Related U.S. Application Data

[63] Continuation of Ser. No. 625,267, Jun. 27, 1984, Pat. No. 4,663,154, which is a continuation of Ser. No. 492,520, May 9, 1983, Pat. No. 4,472,373.

[51] Int. Cl.⁵ .............................................. A61K 7/22
[52] U.S. Cl. ..................................................... 424/54
[58] Field of Search ......................................... 424/54

[56] References Cited

U.S. PATENT DOCUMENTS

| | | | |
|---|---|---|---|
| 1,195,504 | 9/1942 | Shelton | 424/329 |
| 2,295,504 | 9/1942 | Shelton | 424/329 |
| 2,446,792 | 8/1948 | Shelton et al. | 260/295 |
| 2,446,793 | 8/1948 | Shelton et al. | 167/33 |
| 2,446,796 | 8/1948 | Shelton et al. | 167/33 |
| 3,925,543 | 12/1975 | Donohue | 424/52 |
| 3,937,805 | 2/1976 | Harrison | 424/52 |
| 3,937,807 | 2/1976 | Haefele | 424/52 |
| 3,988,435 | 10/1976 | Humbert et al. | 424/54 |
| 4,080,441 | 3/1978 | Gaffar et al. | 424/54 |
| 4,118,474 | 10/1978 | Gaffar et al. | 424/54 |
| 4,241,049 | 12/1980 | Colodney | 424/54 |
| 4,256,731 | 3/1981 | Curtis et al. | 424/54 |
| 4,472,373 | 9/1984 | Ryan | 424/54 |
| 4,663,154 | 5/1987 | Ryan | 424/54 |

*Primary Examiner*—Shep K. Rose
*Attorney, Agent, or Firm*—Douglas C. Mohl; Jack D. Schaeffer; Richard C. Witte

[57] ABSTRACT

Oral compositions such as toothpastes, mouthwashes, lozenges and chewing gum containing an antimicrobial agent which is effective against plaque/gingivitis and mouth odor ar disclosed.

2 Claims, No Drawings

ORAL COMPOSITIONS

This is a continuation of application Ser. No. 625,267, filed on June 27, 1984, now U.S. Pat. No. 4,663,154 which is a continuation of application Ser. No. 432,520, filed on May 9, 1983, now U.S. Pat. No. 4,472,373.

TECHNICAL FIELD

The present invention relates to oral compositions containing an antimicrobial agent, which is either a N-tetradecylpyridinium salt or a N-tetradecyl-4-ethylpyridinium salt, effective against plaque/gingivitis and mouth odor.

BACKGROUND ART

The use of antimicrobial agents to reduce plaque/gingivitis as well as mouth odor has been recognized for many years. Included among references disclosing oral compositions containing antimicrobials are U.S. Pat. No. 3,937,805, Feb. 10, 1976 to Harrison; U.S. Pat. No. 3,937,807, Feb. 10, 1976 to Haefele; U.S. Pat. No. 4,080,441, Mar. 21, 1978 to Gaffar et al; U.S. Pat. No. 4,118,474, Oct. 3, 1978 to Gaffar et al; U.S. Pat. No. 4,241,049, Dec. 23, 1980 to Colodney et al; U.S. Pat. No. 3,925,543, Dec. 9, 1975 to Donohue; and U.S. Pat. No. 4,256,731, Mar. 17, 1981 to Curtis et al.

N-tetradecylpyridinium neohesperidin dihydrochalcone is disclosed in U.S. Pat. No. 3,988,435, Oct. 26, 1976 to Humbert et al as suitable for use in oral products as an antibacterial. The particular antimicrobials of the present invention have also been disclosed among a wide group of materials as useful for a variety of purposes. References making such disclosures are U.S. Pat. No. 2,295,504, Sept. 8, 1942 to Shelton and U.S. Pat. No. 2,446,792, Aug. 10, 1948 to Shelton et al.

While the prior art discloses the use of antimicrobials in oral products, none of the prior art references teach or suggest the superior properties possessed by the present compositions.

Plaque is composed of bacteria and their extracellular by-products that together form a film on tooth surfaces. Bacteria are also involved in the formation of bad breath. Antimicrobials have been shown to be able to kill bacteria in the oral cavity thereby reducing the level of plaque formed and mouth odor.

It has now been found that by using either a N-tetradecylpyridinium salt or N-tetradecyl-4-ethylpyridinium salt superior antiplaque and antigingivitis activity is achieved as well as improved mouth odor control. Although not wishing to be bound by theory, it is believed that this improved performance is the result of achieving a proper balance of adherence to the surfaces of the mouth and release from such surfaces.

It is still a further object of the present invention to provide a method for reducing plaque/gingivitis and control mouth odor.

These and other objects will become more apparent from the detailed description which follows. All percentages and ratios herein are by weight unless otherwise specified.

SUMMARY OF THE INVENTION

The present invention relates to oral compositions which provide antiplaque/antigingivitis benefits while also reducing breath odor comprising:

(a) a safe and effective amount of an antimicrobial selected from the group consisting of N-tetradecylpyridinium salts, N-tetradecyl-4-ethylpyridinium salts and mixtures thereof; and (b) a pharmaceutically acceptable carrier.

DETAILED DESCRIPTION OF THE INVENTION

The compositions of this invention employ a N-tetradecylpyridinium salt and/or a N-tetradecyl-4-ethylpyridinium salt in a pharmaceutically acceptable carrier. These and other components will be described in detail hereinafter.

By "safe and effective amount" as used herein, means sufficient compound to reduce plaque/gingivitis and mouth odor while being safe to the hard and soft tissues of the oral cavity.

By the term "comprising," as used herein, is meant that various additional components can be conjointly employed in the compositions of this invention as long as the pyridinium salt performs its intended functions.

By the term "carrier," as used herein, is meant a suitable vehicle which is pharmaceutically acceptable and can be used to apply the present compositions in the oral cavity.

Pyridinium Salt

The pyridinium salt used in the present invention is either a N-tetradecylpyridinium salt or a N-tetradecyl-4-ethylpyridinium salt. These salts are known in the art as seen by U.S. Pat. No. 2,446,792, Aug. 10, 1948 to Shelton et al and U.S. Pat. No. 2,295,504, Sept. 8, 1942 to Shelton, both incorporated herein by reference. The N-tetradecylpyridinium salt can be represented as follows:

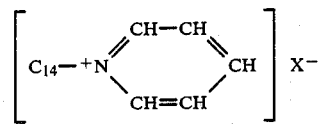

wherein $X^-$ is an acid ion constituent such as fluoride, chloride, bromide, iodide, nitrate, acetate, phenylsulfonate among many others. The preferred ions are the fluoride, chloride, bromide and iodide with chloride being the most preferred.

The tetradecylethylpyridinium salt has the ethyl group at the "4" position on the ring and can be represented similarly

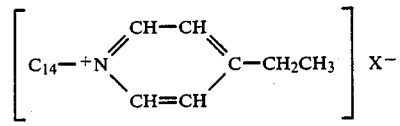

wherein X is as defined above.

The amount of pyridinium salt used in the present compositions can be any amount that is safe to use in the mouth and capable of providing reduced plaque/gingivitis and breath odor. This amount will vary depending on the pharmaceutically acceptable carrier selected but generally is in the range of from 0.001% to about 20%, preferably from about 0.01% to about 7%.

Pharmaceutically Acceptable Carrier

The carrier for the antimicrobial compound can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

Dentifrices preferably contain from about 0.05% to 7% by weight of the antimicrobial component. Dentifrices also contain an abrasive polishing material and typically also contain sudsing agents, flavoring agents and sweetening agents. Toothpaste compositions additionally contain binders, humectants and water.

The dentifrice abrasive, generally has a particle size of from about 0.1 to about 10 microns in diameter and can be any abrasive polishing material which does not excessively abrade tooth dentin. These include, for example, silica, both precipitated and gels, calcium carbonate, dicalcium orthophosphate dihydrate, calcium pyrophosphate, calcium polymetaphosphate and insoluble sodium polymetaphosphate. Preferably, however, the abrasive is one which has a high degree of compatibility with the antimicrobials. These include, for example silica xerogels such as those described in U.S. Pat. No. 3,538,230 to Pader et al, issued Nov. 3, 1970; hydrofluoric acid-treated amorphous silica abrasives such as those disclosed in U.S. Pat. No. 3,862,307 to DiGiulio, issued Jan. 21, 1975; mineral abrasives coated with cationic polymers such as those disclosed by J. J. Benedict in U.S. Pat. No. 4,157,387, issued June 5, 1979; and condensation products of urea and formaldehyde such as those disclosed in Cooley et al, in U.S. Pat. No. 3,070,510, issued Dec. 24, 1972. All of these patents are incorporated herein by reference.

The total amount of abrasive materials in the dentifrice embodiments of this invention can range from about 0.5% to about 95% by weight of the dentifrice. Preferably toothpastes contain from about 6% to about 60% by weight and toothpowders contain from about 20% to about 95% by weight abrasives.

Dentifrice compositions can also contain emulsifying agents. Suitable emulsifying agents are those which are reasonably stable and foam throughout a wide pH range, including non-soap non-ionic, cationic, zwitterionic and amphoteric organic synthetic detergents. Many of these suitable surfactants are disclosed by Gieske et al in U.S. Pat. No. 4,051,234, Sept. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al, U.S. Pat. No. 2,946,725, issued July 26, 1960 and Widder et al, U.S. Pat. No. 3,678,154, issued July 18, 1972 disclose such salts as well as others.

In preparing toothpastes, it is necessary to add some thickening material to provide a desirable consistency. Preferred thickening agents are carboxyvinyl polymers, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols. The humectant can comprise up to about 65% by weight of the toothpaste composition.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Another preferred embodiment of the present invention is a mouthwash composition. Conventional mouthwash composition components can comprise the carrier for the antimicrobial of the present invention. Mouthwashes generally comprise about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water. The amount of antimicrobial agent in mouthwashes is typically from about 0.01 to about 0.5% by weight.

Suitable lozenge and chewing gum components are disclosed in U.S. Pat. No. 4,083,955, Apr. 11, 1978 to Grabenstetter et al, incorporated herein by reference.

An optional ingredient which may be useful in the present compositions is an antistain agent. As with other antimicrobials the materials used in the present compositions may cause staining when used at fairly high levels. Antistain agents include carboxylic acids such as those disclosed in U.S. Pat. No. 4,256,731, May 17, 1981 to Curtis et al, incorporated herein by reference. Other agents include amino carboxylate compounds as disclosed in U.S. Pat. No. 3,937,807, Feb. 10, 1976 to Haefele; dicarboxylic acid esters as disclosed in U.S. Pat. No. 4,080,441, Mar. 21, 1978 to Gaffar et al; and phosphonoacetic acid as disclosed in U.S. Pat. No. 4,118,474, Oct. 3, 1978 to Gaffar et al. All of these patents are also incorporated herein by reference. Many other agents in addition to those discussed herein may also be used. If used the agents are generally in an amount of 0.05% or greater. If The antistain active may be used in the same composition with the pyridinium compound or in a separate composition used sequentially with the pyridinium composition.

The pH of the present cmpositions and/or its pH in the mouth can be any pH which is safe for the mouth's hard and soft tissues. Such pH's are generally from about 3 to about 10, preferably from about 4 to about 8.

METHOD OF MANUFACTURE

The carrier compositions of the present invention can be made using methods which are common in the oral products area.

COMPOSITION USE

The present invention in its method aspect involves applying to the oral cavity safe and effective amounts of the antimicrobial. Generally an amount of at least about 0.001 g. of the antimicrobial is effective.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

An in-vivo gingivitis study was conducted to determine the ability of N-tetradecylpyridinium chloride to reduce gingival bleeding relative to N-cetylpyridinium chloride. The procedure utilized was as follows:

Eighteen male dental students, in the age range of 22–26 years were recruited for the clinical trial. After a thorough prophylaxis and scaling, they were asked to perform optimal oral hygiene for a period of two weeks, using the method of Bass (1954) for toothbrushing and dental floss and interdental wood sticks for interproximal cleansing. This pre-experimental phase was supervised by a registered dental hygienist who also performed the depuration of all the participants. At the end of the pre-experimental phase, the plaque and gingival indices of all participants approached 0. The individuals were then screened for antibiotic usage and the present of unusual oral lesions. The conditions, if present, were recorded.

At the end of the pre-experimental phase, the students were randomly divided into three groups of nine subjects. They were asked to abolish all oral hygiene measures for a period of 21 days during which they rinsed with one of the following solutions.

Group A rinsed twice daily with 15 ml of a flavored alcoholic solution of 0.075% N-cetylpyridinium chloride.

Group B rinsed twice daily with 15 ml of a flavored alcoholic solution containing 0.075% of N-tetradecylpyridinium chloride.

The two daily rinsings were supervised by a registered dental hygienist and timed for 30 seconds between 0800 and 1000 in the morning and 1600 and 1800 in the afternoon on workdays (Saturdays included). On Sundays no product was administered.

Following the three week period of no oral hygiene, the participants again resumed optimal plaque control with mechanical procedures for one week.

At the beginning (day 0), after 7, 14 and 21 days of experimental gingivitis and one week following the reinstitution of oral hygiene measures (day 28), the number of bleeding gingival sites were determined using the technique of Loe and Silness and the reduction relative to the placebo was determined. The reduction for N-tetradecylpyridinium chloride was 63% while the reduction for N-cetylpyridinium chloride was only 35%.

EXAMPLE II

An in-vivo breath odor study was conducted to determine the ability of N-tetradecyl-4-ethylpyridinium chloride (TDEPC) to improve morning breath odor relative to a placebo.

Test Protocol

Panelists discontinued the use of mouthwash and breath mints one week prior to the start of product usage. Initial morning breath odor (IBO) assessments were made by three experts following the one week of discontinued use and prior to any treatments. The restrictions placed on the panelist the morning of the evaluation were: no toothbrushing, no eating or drinking except for water; no smoking, or wearing perfumed products. Based on the IBO grades, a paired breath odor-balanced panel was established (i.e. subjects with IBO grades of 1 were paired together, likewise for 0, 2, 3, 4 grades).

The mouthwashes tested were as follows:

| Component | (%) |
|---|---|
| TDEPC | 0.075 |
| Distilled $H_2O$ | 73.091 |
| Ethanol | 16.250 |
| Glycerin | 10.000 |
| Nonionic Surfactant | 0.120 |
| Benzoic Acid | 0.050 |
| Na Saccharin | 0.055 |
| Flavor | 0.160 |
| Color | 0.044 |
| NaOH(10% Sol.) | 0.155 |
| | 100.000 |

The placebo product was the same except that the TDEPC was not present.

Panelists used their mouthwash treatment twice daily, once in the morning and once in the evening for 1 week. The specified dosage was 15 ml to be used for 30 seconds in the mouth. Panelists were not permitted to rinse with water. During the work week controlled usage was utilized for the morning treatment (5 out of the 14 dosages). The evening and weekend dosages were panelists-administered (9 out of 14 dosages). After one week of treatment a panelist's morning breath was evaluated by expert and consumer judges. The restrictions previously mentioned were required. The consumer-as-judges rated a dynamic breath (panelist was gently breathing) paired comparison for breath preference of an intially balanced pair. Each panelist was then evaluated by an expert for breath quality. The experts assessment was made on a static breath (i.e. the subject holds their breath).

Results/Discussion

Twice daily rinsing with the mouthwash containing TDEPC (0.075 wt. %) provides a significant reduction (95% level) in "morning breath" vs. a placebo based on expert ratings, 1.17 vs. 1.79.

EXAMPLE III

Experiments were conducted with several substituted pyridinium compounds to determine the minimum inhibitory concentration of the compounds in saliva and to determine how long this level or a greater level was present.

Test solutions containing 0.1% w/volume of the following pyridinium compounds in water were prepared:
N-tetradecyl 4-ethylpyridinium chloride ("14/2")
N-dodecyl 4-butylpyridinium chloride ("12/4")
N-decyl 4-hexylpyridinium chloride ("10/6")
N-pentadecyl 4-methylpyridinium chloride ("15/1")

Six panelists were recruited to rinse with 15 ml of each of the above solutions, one solution per day on four different four days. The rinsings were for 30 seconds after which the panelist expectorated the solution into a test tube. The panelists then rinsed with water for 5 seconds, this rinsing taking place 15 seconds after expectorating the pyridinium salt solution. The panelists were then asked to collect 3-5 ml of nonstimulated expectorated saliva at 30, 60, 90, 120 and 180 minutes after sample usage.

Individual saliva samples were thoroughly mixed together after which aliquots were drawn, 2.5 or 3.5 ml, and centrifuged for a total of 30 minutes. The supernatant was then decanted from each sample and analyzed for available pyridinium compound using high performance liquid chromatography. The values (averages) for the compunds at the various times were as follows:

| | μ Molar Concentration | | | | |
|---|---|---|---|---|---|
| | Minutes After Rinsing | | | | |
| Active | 30 | 60 | 90 | 120 | 180 |
| "14/2" | 60.9 | 38.2 | 25.0 | 19.7 | 10.0 |
| "12/4" | 37.4 | 20.3 | 15.6 | 10.3 | 7.1 |
| "10/6" | 24.7 | 17.6 | 11.5 | 8.2 | 6.5 |
| "15/1" | 42.9 | 29.4 | 29.4 | 11.8 | 7.4 |

The minimum inhibitory concentration (MIC) in saliva was also determined for each of the compounds. A quantity of stimulated saliva was vortexed, filtered and then incubated at 37° C., 95% RH and 5% $CO_2$. Solutions of the pyridinium compounds were prepared having a pyridinium concentration of 0.003M and then diluted in sterile, distilled water 1:2 and 1:4.

Saliva for use as inoculum was obtained from five subjects and was then diluted 1:10 in the sterile saliva described above. Sterile saliva, an active and the inoculum were then placed in microtiter plates. Average values from eight serial dilution tests (each performed in duplicate) for each active were obtained. The average MIC values for the actives were as follows:

| Active | MIC $\mu M$ |
|---|---|
| "14/2" | 11.1 |
| "12/4" | 11.5 |
| "10/6" | 13.5 |
| "15/1" | 18.5 |

Using the MIC values and the time/concentration data for the various actives, the following times are obtained (linear regression analysis) for the duration of a MIC value:

| Active | Time Hours |
|---|---|
| "14/2" | 2.80 |
| "12/4" | 2.05 |
| "10/6" | 1.41 |
| "15/1" | 1.71 |

The difference between "14/2" and "12/4" is significant at the 99% level.

What is claimed is:

1. A method of inhibiting plaque comprising the step of contacting plaque in the oral cavity with an effective amount of composition comprising a dentifrice carrier suitable for use in the oral cavity and from about 0.05% to about 7% of an antimicrobial selected from the group consisting of the fluoride, chloride, bromide and iodide salts of N-tetradecyl-4-ethyl pyridinium.

2. An oral composition effective in inhibiting plaque/gingivitis and reducing mouth odor comprising:
    (a) from about 0.05% to about 7% of an antimicrobial selected from the group consisting of the bromide, fluoride, chloride and iodide salts of N-tetradecyl-4-ethyl pyridinium; and
    (b) a pharmaceutically acceptable carrier in the form of a dentifrice.

* * * * *